United States Patent [19]

Wünsch

[11] Patent Number: 4,507,235

[45] Date of Patent: Mar. 26, 1985

[54] METHOD FOR PREPARING PEPTIDES AND INTERMEDIATE PRODUCTS

[75] Inventor: Erich Wünsch, Tutzing, Fed. Rep. of Germany

[73] Assignee: Max-Planck-Gesellschaft zur Förderung der Wissenschaften e.V., Göttingen, Fed. Rep. of Germany

[21] Appl. No.: 586,187

[22] Filed: Mar. 5, 1984

Related U.S. Application Data

[62] Division of Ser. No. 331,311, Dec. 16, 1981, abandoned, which is a division of Ser. No. 145,500, Apr. 29, 1980, Pat. No. 4,368,192.

[30] Foreign Application Priority Data

Apr. 30, 1979 [DE] Fed. Rep. of Germany ....... 2917603
Oct. 25, 1979 [DE] Fed. Rep. of Germany ....... 2943132

[51] Int. Cl.$^3$ ............................................ C07C 103/52
[52] U.S. Cl. ............................................. 260/112.5 R
[58] Field of Search ................................. 260/112.5 R

[56] References Cited

U.S. PATENT DOCUMENTS

| | | | |
|---|---|---|---|
| 3,038,908 | 6/1962 | Beereboon | 260/346.2 |
| 3,579,494 | 5/1971 | Ondetti et al. | 260/112.5 R |
| 3,705,140 | 12/1972 | Bernardi et al. | 260/112.5 R |
| 3,723,406 | 3/1973 | Ondetti et al. | 260/112.5 R |
| 3,734,946 | 5/1973 | Ondetti | 260/112.5 R |
| 3,778,429 | 12/1973 | Ondetti et al. | 260/112.5 R |
| 4,330,466 | 5/1982 | Yanaihara et al. | 260/112.5 R |

OTHER PUBLICATIONS

Chem. Abstr. vol. 91, (1979), 175731.
Chem. Abstr. vol. 92, (1980), 147192.
Chem. Abstr. vol. 95, (1981), 81480.
Chem. Abstr. vol. 95, (1981), 169774.
Chem. Abstr. vol. 85, (1976), 160525.
Chem. Abstr. vol. 95, (1981), 7776.
Chem. Abstr. vol. 94, (1981), 66091.

Primary Examiner—Delbert R. Phillips
Attorney, Agent, or Firm—Morgan, Finnegan, Pine, Foley & Lee

[57] ABSTRACT

Peptides having the carboxyl terminated sequence of the pancreozymin-cholecystokinin 25–33 modified such that the amino acid group 25 carries a strongly basic group, the amino acid group 28 exhibits a hydrophilic character similar to that of the hydroxyamino acids and the amino acid group 31 exhibits a strongly hydrophobic character similar to that of amino acids with aliphatic side chains, and in particular nonapeptides having the sequence H—X—Asp—Tyr(SO$_3$H)—Y—Gly—Trp—Z—Asp—Phe—NH$_2$ wherein X is arginine, homoarginine, norarginine, N$_\epsilon$,N$_\epsilon$-dialkyllysine, N$_\delta$ or N$_\delta$-dialkyl-ornithine, Y is threonine, serine or hydroxy-proline and Z is norleucine, leucine, norvaline or α-amino-butyric acid, possess pronounced pancreozymin activity and can be employed in pharmaceutical preparations for controlling the function of the gall bladder and for controlling the enzyme secretion of the pancreas. Tyrosine-O-sulfate-barium salt and its N-acyl derivatives can be used as intermediate products for the preparation of peptides. For introducing the amino acid group 27 an N-acyltyrosine is reacted with an excess of pyridine—SO$_3$ in a polar organic solvent, the resulting solution is extracted with water, the barium salt of the N-acyl-tyrosine-O-sulfate is precipitated from the aqueous phase by addition of a soluble barium compound, possibly the acyl group is split off in conventional manner, and the resulting tyrosine-O-sulfate-barium salt or its acyl derivative are processed employing the usual methods of peptide synthesis.

5 Claims, No Drawings

METHOD FOR PREPARING PEPTIDES AND INTERMEDIATE PRODUCTS

CROSS-REFERENCES TO RELATED APPLICATIONS

This application is a divisional application of application Ser. No. 331,311, filed Dec. 16, 1981, now abandoned, which in turn is a divisional application of application Ser. No. 145,500, filed Apr. 29, 1980, now U.S. Pat. No. 4,368,192, granted Jan. 11, 1983.

DESCRIPTION

1. Field of the Invention

The present invention relates to the preparation of peptides containing a tyrosine-O-sulfate moiety.

2. Brief Description of the Background of the Invention Including Prior Art

Tyrosine-O-sulfate was discovered as a metabolite in the urine of mammals and was later also discovered as a building block in various biologically active peptides and proteins, for example in gastrines. This amino acid group further provides the "essential" grouping for biological activity in the biologically interesting peptide hormones cholecystokinin-pancreozymin and caerulein. Therefore, it is an important goal of biochemical and in particular peptide-chemical research and of the pharmaceutical development to synthesize such biologically active tyrosine-O-sulfate containing peptides and proteins, respectively.

Biologically active peptides containing tyrosine-O-sulfate have been prepared predominantly by subsequent sulfation of the phenolic group within the peptide with concentrated sulfuric acid or pyridine/SO$_3$ complex. These methods have the disadvantage that to an interfering extent side reactions occur such as sulfonation of the phenolic ring, of the indolyl or imidazolyl groups on the one hand or reactions with the methionine-thioether-grouping, the arginine-guanidine and the primary amido-function on the other hand (J. Am. Chem. Soc. 68,1024 and 1031 (1946)). The additional easily sulfatable hydroxy and amino functions had to be protected. This disadvantage can be avoided if it is achievable to construct such active peptides with tyrosine-O-sulfate as a starting material. This would allow to avoid the limitations on the peptide synthesis imposed by the cited side reactions. An experiment has been reported to build such peptides employing tyrosine-O-sulfate as the potassium sulfate, however neither experimental details nor the results are known (Experientia 28, 7 (1972)).

SUMMARY OF THE INVENTION

1. Purposes of the Invention

It is an object of the invention to provide intermediates and a method for synthesizing peptides containing a tyrosine-O-sulfate group.

2. Brief Description of the Invention

The present invention provides tyrosine-O-sulfate-barium salt and its acyl derivatives which can be prepared by contacting N-acyl-tyrosine with excess pyridine-SO$_3$ in a polar organic solvent or solvent mixture, extracting the solution with water, adding to the resulting aqueous phase a soluble barium compound and separating from the aqueous phase the precipitated barium salt of the N-acyl-tyrosine-O-sulfate. The present invention will be illustrated by a method for preparing pancreozymincholecystokinin active peptides having a modified carboxyl terminated sequence of pancreozymin-cholecystokinin 25-33 wherein the modification comprises the amino acid group 25, which carries a strongly basic group, the amino acid group 28, which exhibits a hydrophilic character similar to that of hydroxyamino acid groups, and the amino acid group 31, which exhibits a strongly hydrophobic character similar to that of amino acid groups having an aliphatic side chain. N-acyl-tyrosine is reacted in a polar solvent with an excess of pyridine-SO$_3$, the resulting solution is extracted with water, the barium salt of the N-acyl-tyrosine-O-sulfate is precipitated from the aqueous phase by adding a soluble barium compound and the resulting N-acyl-tyrosine-O-sulfate-barium salt is processed for obtaining the desired compounds by conventional peptide synthesis methods. The acyl group can be split off from the N-acyl-tyrosine-O-sulfate-barium salt and form tyrosine-O-sulfate-barium salt. The tyrosine-O-sulfate-barium salt can be processed by condensation in accordance with the dicyclohexylcarbodiimide/1-hydroxybenzotriazole method, in accordance with the method via mixed anhydrides or in accordance with the method employing dicylohexylcarbodiimide/N-hydroxysuccinimide.

A nonapeptide can be prepared by condensing tyrosine-O-sulfate-barium salt with H—Y(t—Bu)—Gly—Trp—Z—Asp(OtBu)—Phe—NH$_2$, hydrogenolytically splitting off the benzyloxycarbonyl group from the condensation product; extending the resulting tyrosine-O-sulfate-peptide derivative with B—X(B$_2$)—Asp(OtBu)—OH in accordance with the dicyclohexylcarbodiimide/N-hydroxysuccinimide method to obtain B—X(B$_2$)—Asp(OtBu)—Tyr(SO$_3$Ba$_{\frac{1}{2}}$)—Y(tBu)—Gly—Trp—Z—Asp(OtBu)—Phe—NH$_2$, wherein X is arginine, homoarginine, N$_\epsilon$, N$_\epsilon$-dialkyllysine, N$_\delta$ or N$_\delta$-dialkyl-ornithine, Y is threonine, serine or hydroxy-proline, and Z is norleucine, norvaline, or α-amino-butyric acid. The three benzyloxycarbonyl groups (B) are hydrogenolytically split off from the amino terminated X-group and the tertiary butanol protective groups are split off from the resulting nonapeptide with an acid reagent, preferably trifluoro-acetic acid. A preferred nonapeptide has the sequence H—Arg—Asp—Tyr(SO$_3$H)—Thr—Gly—Trp—Nle—Asp—Phe—NH$_2$.

DESCRIPTION OF INVENTION AND PREFERRED EMBODIMENTS

A nonapeptide which may be prepared in accordance with the present invention may have the general formula H—X—Asp—Tyr(SO$_3$H)—Y—Gly—Trp—Z—Asp—Phe—NH$_2$, wherein X is arginine, homoarginine, norarginine, N$_\epsilon$,N$_\epsilon$-dialkyllysine, N$_\delta$ or N$_\delta$-dialkyl-ornithine, Y is threonine, serine or hydroxyproline and Z is norleucine, norvaline or α-amino-butyric acid, or less preferably leucine.

A preferred sequence is H—Arg—Asp—Tyr (SO$_3$H)—Thr—Gly—Trp—Nle—Asp—Phe—NH$_2$. The peptides are useful as pancreozymin-cholecystokinin active compositions.

The preparation of the peptides according to the present invention employs conventional steps as they are, for example, disclosed in Moroder, L., L. Wilschowitz, E. Jaeger, S. Knof, P. Thamm and E. Wuensch in "Hormonal Receptors in Digestive Tract Physiology" (G. Rosselin et al. eds.), Elsevier/North-Holland Biomedical Press, Amsterdam 1979, Pages 129–135 and also Moroder, L., L. Wilschowitz, E. Jaeger, S. Knof, P. Thamm and E. Wuensch (1979) Hoppe Seyler's Z. Physiol. Chem. 360, 787–790.

A preferred method for making the peptides comprises reacting an N-acyl-tyrosine with excess pyridine-$SO_3$ in a polar organic solvent for introducing the amino acid group 27, extracting the resulting solution with water, adding a soluble barium compound to the aqueous phase and precipitating the barium salt of the N-acyl-tyrosine-O-sulfate, if desired splitting off the acyl group in a conventional way and processing the resulting tyrosine-O-sulfate-barium salt or its acyl derivative by generally known steps of the usual peptide synthesis methods.

Tyrosine-O-sulfate-barium salt and/or an acyl derivative thereof and preferably N-carbobenzoxy-tyrosine-O-sulfatebarium salt is employed as an intermediate in accordance with the present invention.

It is possible to avoid the disadvantages of the prior art by employing the intermediate product of the present invention, the tyrosine-O-sulfate-barium salt and its N-acyl derivatives together with the acyl protective groups usually employed in peptide chemistry and preferably of the N-carbobenzoxy-tyrosine-O-sulfate-barium salt. Thus tyrosine-O-sulfate containing compounds are provided which are useful as starting materials for the synthetic production of peptides. Based on their solubility characteristics they facilitate the isolation of the peptides prepared with them.

Tyrosine-O-sulfate-barium salt has the formula H—Tyr($SO_3Ba_{\frac{1}{2}}$)—OH, the cited carbobenzoxy compound the formula B—Tyr($SO_3Ba_{\frac{1}{2}}$)—O—$Ba_{\frac{1}{2}}$. In these formulas Tyr means tyrosine and B represents the carbobenzoxy group. The abbreviations employed herein correspond to the rules set forth in Houben-Weyl, Methoden der organischen Chemie, 4th edition, Volume 15/1, page 20, publisher Thieme, Stuttgart (1974). Houben-Weyl cites also additional acyl protective groups usual in peptide chemistry. Examples are N-t-butyloxycarbonyl-, N-fluorenyloxycarbonyl- and N-2-nitrophenyl-sulfenyl-tyrosine-O-sulfate-barium salt.

Tyrosine-O-sulfate-barium salt is prepared in accordance with the present invention by reacting an N-acyl-tyrosine with excess pyridine-$SO_3$ in a polar organic solvent or solvent mixture, extracting the resulting solution with water, precipitating the barium salt of the N-acyltyrosine-O-sulfate by addition of a soluble barium compound and splitting off the acyl group, if desired. A preferred organic solvent is pyridine or a mixture of pyridine-dimethylformamide. However other weakly basic or neutral polar organic solvents and solvent mixtures can also be employed. The excess of pyridine-$SO_3$ complex is not critical, a 2 to 6 fold amount can be employed and preferably a 3 to 5 fold amount can be employed relative to the $SO_3$ equivalents. The reaction can be performed at temperatures from about 0° C. to the boiling point of the solvent and preferably at temperatures of from about 20° C. to 80° C. After completion of the reaction the excess pyridine-$SO_3$ complex is separated by cooling and removed from the solution. Then the solution is thinned with water, impurities are extracted with organic solvents such as acetic acid ethyl ester and then a suitable soluble barium compound, preferably barium hydroxide, is added to the aqueous phase. It is preferred to employ a 2 to 3 fold excess of the barium compound.

Excess barium hydroxide can be separated by addition of carbon dioxide, while acidification of the solution is avoided by addition of weak alkaline materials which are preferably organic bases such as pyridine. After removal of the precipitate the acyl group containing barium salt of the tyrosine-O-sulfate is obtained. It can be employed as is for the synthesis of peptides or it can be transformed into the tyrosine-O-sulfate-barium salt. The acyl group is split off in the way usually employed in peptide synthesis, for example in case of a carbobenzoxy group by hydrogenation in the presence of palladium as a catalyst preferably in a reaction medium containing dimethylformamide.

The new barium salts of the present invention are especially suitable for the total synthetic formation of tyrosine-O-sulfate containing peptides and proteins, respectively, since they influence positively the isolation of the peptide derivatives prepared with them. It was surprisingly discovered that the usual methods of peptide synthesis can be employed without splitting off the O-sulfate group. This is valid for example also for the splitting off of the protective groups such as the splitting off of protective groups based on tertiary butanol under acid conditions. This was unexpected, since in the past reference was always made to the instability of tyrosine-O-sulfate against acids.

Typical examples of peptide synthesis methods performable in the presence of the compounds of the present invention without decomposing the same are the condensation in accordance with the dicyclohexylcarbodiimide/1-hydroxybenzotriazole method (DCCD/HOBT-method), the methods via mixed anhydrides for example with pivaloylchloride, chloroformic acid ethyl ester or isobutylester. Another example for a suitable method of synthesis is the dicyclohexylcarbodiimide/N-hydroxysuccinimide method.

The particular usefulness of the intermediate products of the present invention is demonstrated with the aid of the benzyloxycarbonyl group containing barium salt in an example of synthesizing the nonapeptide of the sequence H—Arg—Asp—Tyr($SO_3H$)—Thr—Gly—Trp—Leu—Asp—Phe—$NH_2$. According to the DCCD/HOBT method the barium compound of the present invention was condensed with H—Thr(tBu)—Gly—Trp—Leu—Asp(OtBu)—Phe—$NH_2$ and gave clearly B—Tyr($SO_3Ba_{\frac{1}{2}}$)—Thr(tBu)—Gly—Trp—Leu—Asp(OtBu)—Phe—$NH_2$ (III) with a yield of 70%. The hydrogenolytically splitting off of the benzyloxycarbonyl group from (III) under usual hydrogenation conditions produced H—Tyr($SO_3Ba_{\frac{1}{2}}$)—Thr(tBu)—Gly—Trp—Leu—Asp(OtBu)—Phe—$NH_2$ (IV) with a yield of 96%. A successive extension of the "amino free" tyrosine-O-sulfate peptide derivative (IV) with B—Arg($B_2$)—Asp(OtBu)—OH in accordance with the DCCD/HOSU method for obtaining B—Arg($B_2$)—Asp(OtBu)—Tyr($SO_2Ba_{\frac{1}{2}}$)—Thr(tBu)—Gly—Trp—Leu—Asp(OtBu)—Phe—NH. (V) had a yield of 96%. The hydrogenolytically splitting off of the three benzyloxycarbonyl groups from the amino terminated arginine group at a pH of about 6 provided the desired nonapeptide derivative (VI), i.e. H—Arg—Asp(OtBu)—Tyr($SO_3H$)—Thr(tBu)—Gly—Trp—Leu—Asp(OtBu)—Phe—$NH_2$ with 83% yield.

Despite the numerous references in the prior art to the acid instability of tyrosine-O-sulfate and its peptides also the last step was successful in the preparation of the pancreozymin-cholecystokinin analog, i.e., the splitting off of the protective groups based on tertiary butanol. The feared simultaneous partial splitting off of the sulfate-semi-ester grouping was not observed. For the splitting off of the protective groups the acid means known for this purpose, are suitable, and trifluoroacetic acid of from about 70 to 90 percent concentration is preferred. It is preferred to add a cation captor such as, for example, 2-methylindol.

EXAMPLE 1

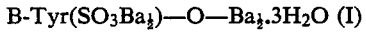
B—Tyr($SO_3Ba_{\frac{1}{2}}$)—O—$Ba_{\frac{1}{2}}$.$3H_2O$ (I)

12.7 g (40.3 mmole) B—Tyr—OH in pyridine are contacted with 25.8 g (161.1 mmole) pyridine-$SO_3$ complex. The suspension is heated to 60° C. and agitated at this temperature until the complex is dissolved (about ½ hour). The solution is then cooled to 0° C. and filtered, the filtrate is concentrated in vacuum and filtered again in order to separate the excess of the complex. Then the solution is thinned with water and extracted twice with acetic acid ethyl ester and the separated aqueous phase is saturated with nitrogen and dependent on the amount of the complex previously separated from about 2 to 3 equivalents of barium hydroxide are added.

The precipitate is sucked off and the excess of barium hydroxide is removed by introduction of carbon dioxide. Addition of pyridine prevents a lowering of the pH to below 7.

After filtration the solution is concentrated to about 100 ml and the product is precipitated with ethanol. Chromatographically pure in n-BuOH/AcOH/$H_2O$/acetic acid ethyl ester (3:1:1:5).

$[\alpha]_{546}^{20}$: +22.7° and $[\alpha]_D^{20}$: +18.9° (c=1, in DMF). Yield: 21.34 g (91 percent of theoretical).

$C_{17}H_{15}NO_8SBa.3H_2O$ (584.80): Calculated: C: 34.92, H: 3.62, N: 2.39, Ba: 25.88, Found: C: 34.87, H: 3.10, N: 2.20, Ba: 23.20.

Calculated residue: 39.9 percent (as $BaSO_4$). Found ignition residue 40.5 percent (as $BaSO_4$).

EXAMPLE 2

H—Tyr($SO_3Ba_{\frac{1}{2}}$)—OH.$H_2O$ (II)

5 g (8.55 mmole) B—Tyr($SO_3Ba_{\frac{1}{2}}$)—O—$Ba_{\frac{1}{2}}$.$3H_2O$ are as usual hydrogenated in the presence of a palladium catalyst in dimethylformamide. After completion of the reaction the filtrate is concentrated in vacuum and the residue is dissolved in water. The insoluble materials are filtered off and the product is precipitated with ethanol. The product is dissolved in water and the pH is brought to 6.5 by introducing carbon dioxide. The precipitate ($BaCO_3$) is removed by filtration and the filtrate is concentrated and finally the product is precipitated with ethanol. Chromatographically pure in n-BuOH-/AcOH/$H_2O$/acetic acid ethyl ester (3:1:1:5): melting point 232° C.

$[\alpha]_D^{20}$: −24.8° and $[\alpha]_{546}^{20}$: −29.6° (c=1, in DMF/$H_2O$; 95:5 by volume).

Yield: 2.6 g (84 percent of theoretical).

$C_9H_{10}NO_6SBa_{0.5}.H_2O$ (346.94): Calculated: C: 31.15, H: 3.48, N: 4.04, Found: C: 30.99, M: 3.12, N: 3.96.

Residue: calculated: 32.18 percent, found: 33.64 percent.

EXAMPLE 3

A.

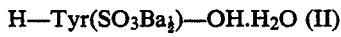
B—Tyr($SO_3Ba_{\frac{1}{2}}$)—Thr(tBu)—Gly—Trp—Leu—Asp(OtBu)—Phe—$NH_2$ (III)

0.62 ml (0.48 mmole) of a 0.77 n HCl solution in dioxane is added drop by drop to a solution of 0.28 g (0.48 mmole) B—Tyr($SO_3Ba_{\frac{1}{2}}$)—$OBa_{\frac{1}{2}}3H_2O$ in dimethylformamide. Under agitation 0.35 g (0.40 mmole) 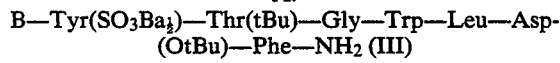
H—Thr(tBu)—Gly—Trp—Leu—Asp(OtBu)—Phe—$NH_2.H_2O$, 70 mg (0.52 mmole) 1-hydroxybenzotriazole and finally, at −10° C., 99 mg (0.48 mmole) of dicyclohexylcarbodiimide are added. After 6 hours at −4° C. and 6 hours at room temperature the solvent is removed by vacuum and the residue is digested with ether. The raw product is taken up with dimethylformamide, the insoluble parts are filtered off and the product is precipitated with water. The product is again precipitated from a methanol solution with ether after the insoluble had been filtered off.

Chromatographically pure in n—BuOH/AcOH/-$H_2O$/acetic acid ethyl ester (3:1:1:5); melting point: 168° C. (decomposition).

$[\alpha]_{546}^{20}$: −22.7° (c=1, in dimethylformamide), $[\alpha]_D^{20}$: −18.8°.

$C_{61}H_{78}N_9O_{16}SBa_{0.5}$(1294.11): Calculated: C: 56.62, H: 6.08, N: 9.79, Found: C: 56.64, H: 6.21, N: 9.87.

B.

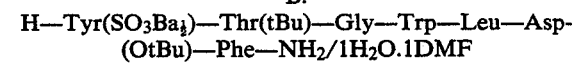
H—Tyr($SO_3Ba_{\frac{1}{2}}$)—Thr(tBu)—Gly—Trp—Leu—Asp(OtBu)—Phe—$NH_2$/$1H_2O$.1DMF 4.07 g (3.14 mmole) B—Tyr($SO_3Ba_{\frac{1}{2}}$)—Thr(tBu)—Gly—Trp—Leu—Asp—(OtBu)—Phe—$NH_2$ are as usual hydrogenated in the presence of palladium in dimethylformamide. After removal of the catalyst the solvent is evaporated in vacuum and the residue is triturated with ether.

Chromatographically pure in n—BuOH/AcOH/-$H_2O$/acetic acid ethyl ester (3:1:1:5), melting point 178° C. (decomposition).

$[\alpha]_D^{20}$: −29.85° and $[\alpha]_{546}^{20}$: −36° (c=1, in DMF).

Yield: 3.72 g (96 percent of theoretical).

$C_{53}H_{72}N_9O_{14}SBa_{0.5}.1H_2O$. 1 DMF (1235.10); Calculated: C: 54.46, H: 6.61, N: 11.34, Found: C: 54.70, H: 6.73, N: 11.34.

C.

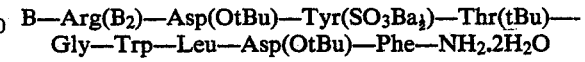
B—Arg($B_2$)—Asp(OtBu)—Tyr($SO_3Ba_{\frac{1}{2}}$)—Thr(tBu)—Gly—Trp—Leu—Asp(OtBu)—Phe—$NH_2.2H_2O$ 0.36 g (3.16 mmole) N-hydroxysuccinimide and at −20° C. 0.63 g (3.04 mmole) dicyclohexylcarbodiimide are added to 3 g (2.43 mmole) H—Tyr($SO_3Ba_{\frac{1}{2}}$)—Thr(tBu)—Gly—Trp—Leu—Asp(OtBu)—Phe—$NH_2.1-H_2O$ and 2.18 g (2.92 mmole) B—Arg($B_2$)—Asp(OtBu)—OH in dimethylformamide. After 24 hours at 4° C. and 24 hours at room temperature the reaction mixture is filtered from the precipitated urea and concentrated in vacuum. The residue is reprecipitated twice from dimethylformamide-ether.

Chromatographically pure in n-BuOH/AcOH/-$H_2O$/acetic acid ethyl ether (3:1:1:5); melting point 190° to 195° C.

$[\alpha]_D^{20}$: −14.3° and $[\alpha]_{546}^{20}$: −17.3° (c=1, in DMF).

D.

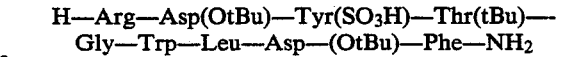
H—Arg—Asp(OtBu)—Tyr($SO_3H$)—Thr(tBu)—Gly—Trp—Leu—Asp—(OtBu)—Phe—$NH_2$ 3.7 g (1.9 mmole) B—Arg($B_2$)—Asp(OtBu)—Tyr(-$SO_3Ba_{\frac{1}{2}}$)—Thr—(tBu)—Gly—Trp—Leu—Asp(OtBu)—Phe—$NH_2.2H_2O$ were as usual hydrogenated in the presence of palladium in a solution of dimethylformamide containing 26.34 ml 0.143 n HCl in MeOH (theor. 26.87 ml) at pH 6.

After removal of the catalyst the product was precipitated with water containing triethylamine. The precipitate was reprecipitated from dimethylformamide-water and carefully washed with water.

Chromatographically pure in n-BuOH/AcOH/H$_2$O/acetic acid ethyl ester (3:1:1:5), melting point 208° C. (decomposition).

$[\alpha]_{546}^{20}$: −25.5° and $[\alpha]_D^{20}$: −21.2° (c=1, in DMF).

Yield: 2.24 g (83 percent of theoretical).

C$_{67}$H$_{97}$N$_{14}$O$_{18}$S (1418.7): Calculated: C: 56.72, H: 6.89, N: 13.82, Found: C: 56.63, H: 6.92, N: 13.47.

EXAMPLE 4

In accordance with the method of the present invention the following compound was prepared:

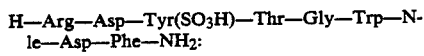

H—Arg—Asp—Tyr(SO$_3$H)—Thr—Gly—Trp—Nle—Asp—Phe—NH$_2$:

Aminoacid analysis (calculated values in brackets) of the acid hydrolysate (6 m HCl/110° C./24 hours with addition of 2.5 percent mercapto-acetic acid):

Arg 1.00[1] Asp 1.92[2] Tyr 1.00[1] Thre 1.03[1] Gly 0.98[1] Trp 0.91[1] Nle 1.02[1] Phe 1.00[1];

of the AP-M disintegration:

Arg 1.00[1] Asp 1.96[2] Tyr(SO$_3$H) 0.98[1] Thr 1.05[1] Gly 1.00[1] Trp 1.00[1] Nle 1.01[1] Phe 1.00[1];

thin layer chromatography (HPTLC-ready to use plates silicagel 60, Merck AG, Darmstadt, Germany) uniform in n-butanol/acetic acid/pyridine/water (60:6:40:24); uniform after high pressure liquid chromatography [column: μ-Bondapak C 18; eluent: 29% acetonitrile and 71% 0.01 molar ammonium acetate buffer, pH 4.0; isocratic] and carrierless electrophoresis [Chamber electrolyte: 0.1 molar ammonium acetate buffer, pH 8.3; electrode distance 50 cm at 1500 volts]; Tyr/Trp=0.0 (according to the UV determination).

What is claimed is:

1. In the method of preparing peptides containing a tyrosine-O-sulfate moiety the improvement comprising the use of tyrosine-O-sulfate barium salt or a N-acyl derivative thereof in said synthesis.

2. The improvement of claim 1 wherein said barium salt is N-carbobenzoxy-tyrosine-O-sulfate barium salt.

3. The improvement of claim 1 wherein said barium salt is N-t-butyloxycarbonyl-tyrosine-O-sulfate barium salt.

4. The improvement of claim 1 wherein said barium salt is N-fluorenyloxycarbonyl-tyrosine-O-sulfate barium salt.

5. The improvement of claim 1 wherein said barium salt is N-2-nitrophenylsulfenyl-tyrosine-O-sulfate barium salt.

* * * * *